United States Patent
Li et al.

(10) Patent No.: US 6,506,341 B2
(45) Date of Patent: Jan. 14, 2003

(54) CHEMILUMINESCENCE DETECTION APPARATUS

(75) Inventors: Leping Li, Poughkeepsie, NY (US); James A. Gilhooly, Saint Albans, VT (US); Clifford O. Morgan, III, Burlington, VT (US); Cong Wei, Poughkeepsie, NY (US); Werner Moser, Gebertingen (CH); Matthias Kutter, Staefa (CH); Joseph Knee, Cromwell, CT (US); Walter Imfeld, Zurich (CH); Bruno Greuter, Wolfhausen (CH); Heinz Stuenzi, Hombrechtiken (CH)

(73) Assignees: International Business Machines Corporation, Armonk, NY (US); ECO Physics AG, Duernten (CH)

( * ) Notice: Subject to any disclaimer, the term of this patent is extended or adjusted under 35 U.S.C. 154(b) by 0 days.

(21) Appl. No.: 09/129,003

(22) Filed: Aug. 4, 1998

(65) Prior Publication Data

US 2001/0007772 A1 Jul. 12, 2001

Related U.S. Application Data

(63) Continuation-in-part of application No. 09/073,604, filed on May 6, 1998, now Pat. No. 6,126,848.

(51) Int. Cl.⁷ .................... H01L 21/302; G01N 21/00
(52) U.S. Cl. ................ 422/52; 436/172; 216/85; 216/89; 438/692; 438/693
(58) Field of Search .............. 422/52; 436/172, 436/113; 216/60, 85, 88, 89; 438/692, 693, 7

(56) References Cited

U.S. PATENT DOCUMENTS 3,882,028 A    5/1975    Zolner
3,904,371 A  * 9/1975    Neti et al. .................. 436/113
3,963,928 A    6/1976    Zolner
4,193,963 A  * 3/1980    Bruening et al. ............. 422/52
4,236,895 A  * 12/1980   Stahl .......................... 436/116
4,268,279 A    5/1981    Shindo et al.
4,333,735 A    6/1982    Hardy et al.
4,754,089 A    6/1988    Matson et al.
5,514,205 A  * 5/1996    Awaji ........................... 96/152
5,931,722 A    8/1999    Ohmi et al.
6,007,408 A    12/1999   Sandhu
6,066,564 A  * 5/2000    Li et al. ...................... 438/692
6,126,848 A  * 10/2000   Li et al. ...................... 216/85
6,296,806 B1   10/2001   Kishkovich et al.

FOREIGN PATENT DOCUMENTS

| JP | 06-318583 | 11/1994 |
| JP | 07-221099 | 8/1995 |
| JP | 08-064561 | 3/1996 |
| JP | 08-162431 | 6/1996 |
| WO | WO 9607469 | 3/1996 |

* cited by examiner

Primary Examiner—Lyle A. Alexander
(74) Attorney, Agent, or Firm—Jay H. Anderson; Tiffany L. Townsend

(57) ABSTRACT

An apparatus is described for detecting the presence of a gaseous chemical produced during a chemical-mechanical polishing operation. The apparatus includes a catalytic converter, a reaction chamber and a light sensor. The catalytic converter, heated to about 800° C. converts the chemical to a different chemical product. The reaction chamber produces an excited species; the pressure in the reaction chamber is maintained sufficiently low to substantially avoid collisional deactivation of the excited species, so as to permit real-time detection of the chemical. A light signal from the excited species is input to the light sensor. An output from the light sensor corresponds to the real-time detection of the chemical, thereby permitting real-time control of the chemical-mechanical polishing operation.

7 Claims, 2 Drawing Sheets

CHEMILUMINESCENCE DETECTION APPARATUS

This application is a continuation-in-part of application No. 09/073,604 filed May 6, 1998, now U.S. Pat. No. 6,126,848.

FIELD OF THE INVENTION

This invention is directed to semiconductor processing and more particularly to the detection of the endpoint for removal of one film overlying another film.

BACKGROUND OF THE INVENTION

In the semiconductor industry, critical steps in the production of integrated circuits are the selective formation and removal of films on an underlying substrate. The films are made from a variety of substances, and can be conductive (for example metal or a magnetic ferrous conductive material) or non-conductive (for example an insulator). Conductive films are typically used for wiring or wiring connections. Non-conductive or dielectric films are used in several areas, for example as interlevel dielectrics between layers of metallization, or as isolations between adjacent circuit elements.

Typical processing steps involve: (1) depositing a film, (2) patterning areas of the film using lithography and etching, (3) depositing a film which fills the etched areas, and (4) planarizing the structure by etching or chemical-mechanical polishing (CMP). Films are formed on a substrate by a variety of well-known methods, for example physical vapor deposition (PVD) by sputtering or evaporation, chemical vapor deposition (CVD), plasma enhanced chemical vapor deposition (PECVD). Films are removed by any of several well-known methods, for example chemical-mechanical polishing (also known as CMP), dry etching such as reactive ion etching (RIE), wet etching, electrochemical etching, vapor etching, and spray etching.

It is extremely important with removal of films to stop the process when the correct thickness has been removed (the endpoint has been reached). With CMP, a film is selectively removed from a semiconductor wafer by rotating the wafer against a polishing pad (or rotating the pad against the wafer, or both) with a controlled amount of pressure in the presence of a chemically reactive slurry. Overpolishing (removing too much) of a film results in yield loss, and underpolishing (removing too little) requires costly rework (redoing the CMP process). Various methods have been employed to detect when the desired endpoint for removal has been reached, and the polishing should be stopped.

The prior art methods for CMP endpoint detection suitable for all types of films involve the following types of measurement: (1) simple timing, (2) friction or motor current, (3) capacitive, (4) optical, (5) acoustical, and (6) conductive.

An exception to the above is U.S. Pat. No. 5,399,234 to Yu et al, in which a chemical reaction is described between potassium hydroxide in the polishing slurry and the layer being polished. The endpoint for polishing is monitored by sending acoustic waves through the slurry and detecting changes in the acoustic velocity as the concentration of reaction product (thought to be silanol in the case of polishing silicon dioxide) from the layer being polished decreases upon reaching an underlying polish stop layer.

These prior art methods each have inherent disadvantages such as inability for real-time monitoring, the need to remove the wafer from the process apparatus (not in-situ), or a lack of sensitivity.

These disadvantages have been overcome with an in-situ endpoint detection scheme for conductive films as described in U.S. Pat. No. 5,559,428 to Li et al titled "In-Situ Monitoring of the Change in Thickness of Films," however a suitable endpoint detection for non-conductive films has yet to be described.

Thus, there remains a need for an in-situ, real-time endpoint detection scheme suitable for use with all types of films. Such a scheme should have high detection sensitivity and extremely fast response time, preferably less than 1 or 2 seconds.

In accordance with the above listed and other objects, an apparatus for detecting the presence of a chemical in a gaseous state, having:

a) a catalytic converter, having at least one input and at least one output, wherein the chemical to be detected is one of the at least one inputs;

b) a reaction chamber, having at least one input and at least one output, wherein one of the at least one outputs from the catalytic converter is one of the at least one inputs;

c) a light sensor having at least one input, wherein one of the at least one outputs from the reaction chamber is one of the at least one inputs is described.

SUMMARY OF THE INVENTION

It is therefore an object of the present invention to provide an apparatus for detecting the endpoint for removal of any type of film overlying another film.

Another object of the present invention is to provide for in situ endpoint detection as the film is being removed.

Yet another object is to provide endpoint detection with high detection sensitivity and extremely fast response time.

BRIEF SUMMARY OF THE DRAWINGS

These and other features, aspects, and advantages will be more readily apparent and better understood from the following detailed description of the invention, in which.

DETAILED EMBODIMENT

Figure 1:
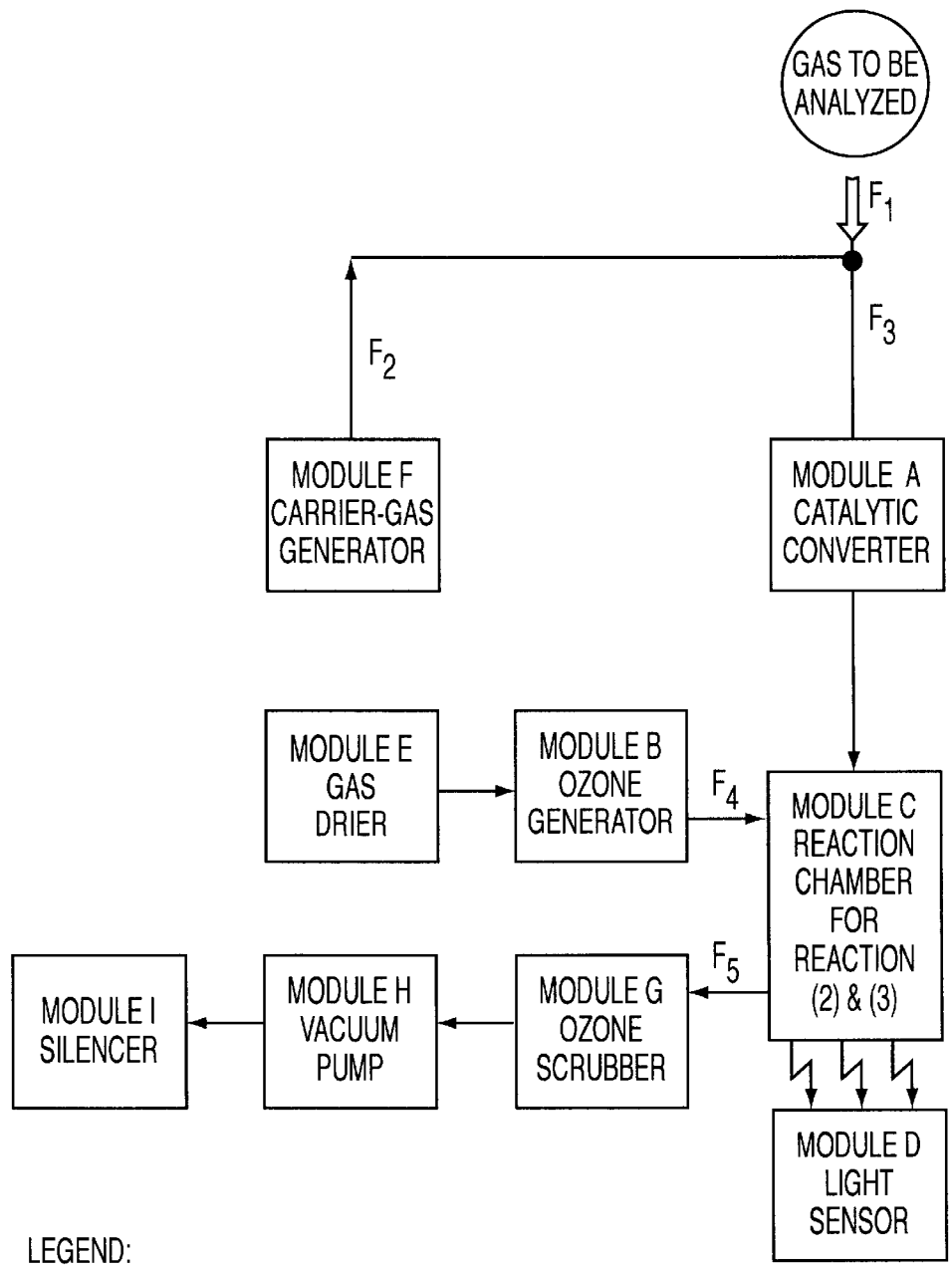
FIG. 1 shows a gas flow of the gas to be analyzed using the apparatus of the instant invention.

The present invention is described herein in the context of chemical-mechanical polishing merely as a specific example, and is not meant to limit applicability of the invention to semiconductor technology. Those skilled in the art will understand that the invention is broadly applicable to any process in which it is desirable to detect the endpoint for removal of a target film overlying a stopping film, by (a) removing the target film with a process that selectively generates a chemical reaction product with one of the stopping film and the target film; (b) converting the chemical reaction product to a separate product; (c) producing an excited gas molecules from the separate product; and (d) monitoring the level of light emitted from the excited gas molecules as the target film is removed.

It has been discovered that when chemically-mechanically polishing a substrate with a target film of oxide ($SiO_2$) over a stopping film of nitride ($Si_3N_4$) with a slurry containing potassium hydroxide (KOH), a chemical reaction occurs when the oxide/nitride interface is reached, resulting in the production of ammonia ($NH_3$). More specifically, the slurry used is a mixture of fumed silica, water, and KOH, with a pH of about 10.5. When polishing oxide, the following reaction occurs:

$$SiO_2 + 2\ KOH + H_2O \rightarrow K_2SiO_3 + 2\ H_2O$$

When polishing nitride, the following reaction occurs:

$$Si_3N_4 + 6\ KOH + 3H_2O \rightarrow 3K_2SiO_3 + 4\ NH_3$$

The ammonia produced is dissolved in the slurry, and because of the relatively high pH it exists primarily in the form of $NH_3$ rather than $NH_4^+$. Thus the presence of ammonia in the slurry indicates that the underlying nitride film has been reached and polished, and the endpoint for removal of the oxide film can be determined by monitoring the level of ammonia in the slurry. Once the endpoint is reached, the polishing should be stopped.

More generally, the endpoint for removal of any non-nitride-containing film overlying a nitride-containing film can be detected by monitoring the level of ammonia in the slurry. Conversely, the endpoint for removal of a nitride-containing film overlying a non-nitride-containing film can also be detected in a similar manner, with a marked decrease in the presence of ammonia indicating the endpoint.

Even more generally, the endpoint for removal of any film overlying another film can be detected by monitoring the level of a chemical reaction product in the slurry as a component of the slurry reacts selectively with one of the films (either the overlying or underlying film). The reaction described above producing ammonia will be discussed as follows but is not intended to limit the scope of the invention to that particular embodiment. In order to implement the above discovery concerning the production of ammonia in an environment suitable for manufacturing, in-situ real time (i.e. while the wafer is being polished) slurry collection and sampling is required. Preferably, the collection and sampling provide a rapid response with high sensitivity (to ammonia) and minimizes the effect of interference from other substances in the slurry and in the surrounding air.

In the current example, in order to detect and monitor ammonia in a gaseous form, thus enabling methods such as mass spectroscopy, slurry from a polishing apparatus is pumped through an ammonia extraction unit (not shown). The ammonia-containing gas stream can be analyzed and monitored for endpoint detection for removal of the target film. Gas phase chemical analysis, such as standard mass spectroscopy can be highly sensitive and have a fast response time, which would be desirable for endpoint detection. However, with slurry sampling, there is substantial interference from water vapor which is only 1 atomic mass unit (AMU) higher and present in abundance. During the electron impact ionization, water can lose a hydrogen resulting in a $OH^+$ion which has a mass identical to $NH3^+$. Thus the ammonia signal from the slurry can be very effectively masked, and endpoint detection becomes impossible.

Nitric Oxide Conversion

The interference of the water fragment $OH^+$ can be circumvented by converting the ammonia in the ammonia-containing gas stream from the extraction unit (not shown) to a separate product which has a different mass than $OH^+$, and indirectly detecting the ammonia by detecting the separate product. An example is converting the ammonia to nitric oxide (NO) using a catalytic converter.

An ammonia-containing gas stream enters the converter (module a in FIG. 1) for example an array of stainless steel tubing having a sufficiently large surface area for a sufficient amount of gas to be converted, which is heated to 800 C. The conversion, known as the Oswald process, is described by the formula $$4\ NH_3(g) + 5\ O_2\ (g) \rightarrow 4\ NO\ (g) + 6H_2O\ (g).$$

The carrier gas for the stream entering the converter can be dry air or other suitable medium, because the nitrogen isotope $(_7N^{15})_2$ will not mask NO using the chemiluminescence method described below.

Chemiluminescence

The phenomenon of chemiluminescence occurs when an excited molecule, produced by a chemical reaction, emits light in the transition from an excited high energy state to a low energy state. Chemiluminescence can be used to detect the presence of ammonia (indirectly by detecting nitric oxide) in this case according to the following:

$$NO(g) + O_3\ (g) \rightarrow NO_2^*(g) + O_2 \qquad (1)$$

$$NO_2^*(g) \rightarrow NO_2\ (g) + h\nu \qquad (2)$$

where the emitted light (photons) are detected by a highly sensitive photomultiplier within a selective spectrum (frequency/wavelength) range. More information on this process and a general method of use and an apparatus are available in Application No. 09/073,604 field May 8, 1998, now U.S. Pat. No. 6,126,848, "Indirect Endpoint Detection by Chemical reaction and chemiluminescence", by Li et al. and incorporated by reference in its entirety.

For optimally sensitive chemiluminescence detection, the pressure of the reaction chamber for reactions (1) and (2) must be kept low. When the pressure in the reaction chamber is low the signal loss due to collisional deactivation may be minimized. It is assumed that the reaction chamber will be able to maintain an environment within the chamber that is conducive to the reactions taking place inside the chamber for the period of time necessary.

There are many separate modules in a device that detects chemiluminescence. One module is a carrier gas generator, module f in FIG. 1. Module f generates the gas that is used as a carrier for the gas to be analyzed and forms the input to the catalytic converter, module a. A NO containing gas stream exiting a catalytic converter (Module a) then enters the reaction chamber, module c, through a flow restrictor (not shown), and is mixed with ozone, generated in module b, (which is controlled by another flow restrictor, which is also not shown) in the reaction chamber, module c. The ozone is produced by conventional means. In a preferred embodiment, a gas drier, module e, facilitates the formation of the ozone in the ozone generator.

In the reaction chamber, module c, NO and $O_3$ react as shown above to produce excited $NO_2^*$ gas, which emits light in a broad band centered at 1200 nm. A light sensor, module d, preferably a very sensitive photomultiplier detects the emission through a color filter used to reject photons with undesired wavelengths. The light sensor is operated in photon counting mode and is controlled by microprocessor (not shown). The analyzer (for example, from ECO PHYSICS AG, Duernten, Switzerland) may output several types of signals. In this embodiment of the present invention, an analog output signal is implemented for quick prototyping. The output signal is converted by the microprocessor from the raw counting signal. The computer monitors the analog NO chemiluminescence signal by an analog to digital conversion (for example with a MIO-16H-9 multifunction DAQ card from National Instruments) and controls the polishing process using an output connection to the polishing machine (not shown).

Note that the chemiluminescence method described is not restricted to use with monitoring the endpoint for CMP. If an overlying film is being removed from an underlying film by etching, for example dry etching (e.g. reactive ion etching), an underlying film (i.e. etch stop) may be selected which generates a marker chemical reaction product upon contact with the etchants. The reaction products of the etching process can be sampled by this method in order to monitor the level of the marker chemical reaction product.

Additionally, any apparatus developed would have to take into consideration the very limited free space within the current generation of polishing machines. There is minimal free area around the wafer being polished and therefore any chemiluminescence detector would have to either be very small or distant from the polishing machine. It is possible with the current invention to have the detector distant from the polishing machine. When the detector is distant from the polishing machine then it must be possible to continuously take samples and transport them to the detector. In a preferred embodiment, the chemiluminescence detection apparatus is at most about 8 meters from the polishing machine.

We disclose and teach an apparatus, a chemiluminescence detection apparatus (CLD), that is able to generally detect processes that involve producing ammonia and $NO_x$, (where x is 1 or 2). Specifically, we disclose an apparatus that is able to detect NO at the level required for endpoint and real time control of CMP processes. FIG. 1 shows a gas flow diagram for the embodiment of the instant invention, for use in detecting endpoint in a CMP process.

In FIG. 1, the gas flow parameters, F1 to F5, are identified. The parameters are controlled by the end user. Preferably, the carrier gas flow, F2 from module f is high compared with the flow F1 from the gas that is to be analyzed. Also in a preferred embodiment, the pressure of the gas at F5, flowing from module e and module f respectively, to module c, would be the lowest pressure in the system, prior to module g.

As stated above, a CLD may be divided into a number of components or modules. A CLD should minimally contain each of the following, which have been described above:

a) a catalytic converter (module a),
b) an ozone generator (module b),
c) a reaction chamber (module c), and
d) a light sensor (module d).

Optimally, a CLD would also contain:

e) a gas drier (module e),
f) a carrier gas generator (module f),
g) an ozone scrubber (module g),
h) a vacuum pump (module h), and
i) a silencer (module i).

Modules g–i treat the module c, reaction chamber, products prior to discarding the gases. It is preferable to treat the module c products so as to at least remove the residual ozone introduced into the system.

It should be noted that there are additional, unidentified, electronic components/sections that facilitate the communication between the different modules. The electronics may also include sensors, like temperature and pressure sensors, that insure that the modules are operating within specified norms. In a preferred embodiment the electronic components/sections would be controlled by a microprocessor. Also, in a preferred embodiment, the light sensor would feed information directly to a microprocessor which could arrest the CMP process when an endpoint condition has been detected. In a more preferred embodiment, the CLD would be able to interface with other components involved with the CMP process like the CMP control computer, probes and interface boxes. There are many configurations that the above identified modules could be arranged. The only restriction on the configurations is that the reactions in modules a, b and c flow in the order identified in FIG. 1 and with the inputs shown supra in FIG. 1.

Figure 2A:
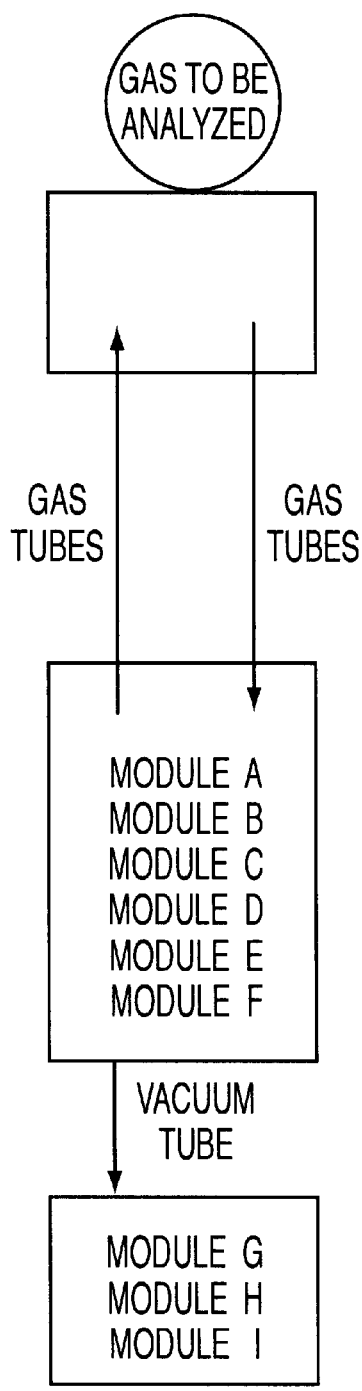
FIGS. 2(a) and (b) show two possible configurations of the modules that form the apparatus of the instant invention.
Figure 2B:
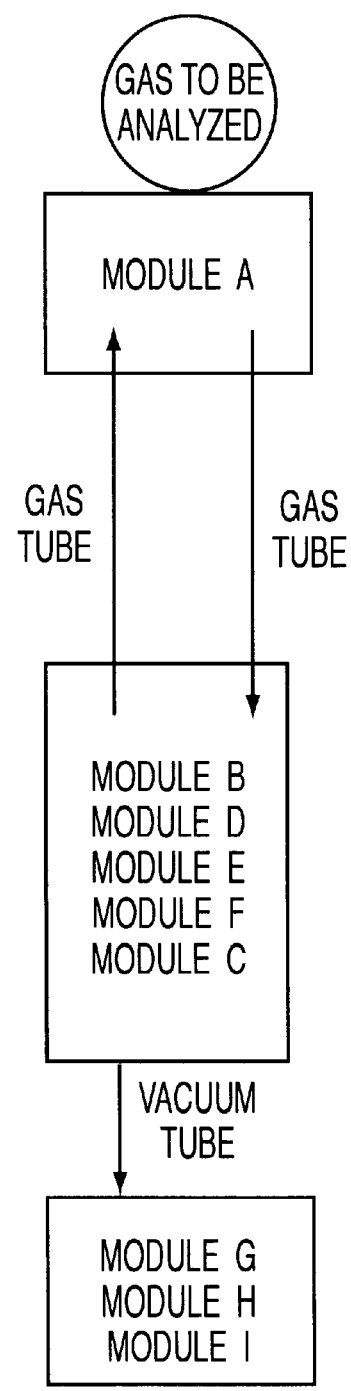

Two possible configurations are shown in FIGS. 2A and 2B. FIG. 2A shows a CLD configuration where modules a–f are located at a distance from the polishing machine and are connected by an appropriate tubing scheme, like gas tubes. Preferably the distance is at most about 8 meters. The gas recovery modules, modules g–i, receive the gases from the reaction chamber, module c. FIG. 2B shows a CLD configuration where the catalytic converter (module a) is located at or very near the polishing machine and modules c,b,d,e, and f are located at a distance from the polishing machine. In this configuration, in addition to the tubing needed for the gas to flow between the polishing machines and the catalytic converter, module a, there must also be communication between module a and module b, c, d, e and f. In this case, the gas transportation can be accelerated significantly with long tubing. As in FIG. 2A, the gas recovery modules g–i, recover the gas products from the reaction chamber, module c.

While the invention has been described in terms of specific embodiments, it is evident in view of the foregoing description that numerous alternatives, modifications and variations will be apparent to those skilled in the art. Thus, the invention is intended to encompass all such alternatives, modifications and variations which fall within the scope and spirit of the invention and the appended claims.

What is claimed:

1. An apparatus for performing a chemical-mechanical polishing process including removing a target film overlying a stopping film and for providing real-time control of the process by detecting the presence of a chemical in a gaseous state to yield a process endpoint signal, the chemical being selectively generated during the polishing process in a slurry as a reaction product with one of the stopping film and the target film, the apparatus comprising:

a collector for collecting the slurry used in the chemical-mechanical polishing process, the slurry having the chemical dissolved therein;

a gas extractor for extracting the chemical as a gas from the slurry;

a catalytic converter for converting the chemical to a different chemical product, said catalytic converter having a heater for heating the converter to about 800° C. to perform the converting and having at least one input and at least one output, wherein the chemical to be detected is an input of the catalytic converter;

a gas generator for generating a reactive gas;

a reaction chamber for producing an excited species in the chemical product by a reaction with the reactive gas, the reaction chamber having at least one input and at least one output, wherein the chemical product is an output of the catalytic converter and is an input of the reaction chamber, and a pressure in the reaction chamber is maintained sufficiently low to substantially avoid collisional deactivation of the excited species, so as to permit real-time detection of the chemical;

a light sensor for monitoring a level of light emitted from the excited species as the target film is removed, said light sensor having at least one input and at least one output, wherein
- a light signal from the excited species is an output of the reaction chamber and is an input of the light sensor, and
- an output of the light sensor corresponds to the real-time detection of the chemical, so that the output of the light sensor is the process endpoint signal; and a controller for providing real-time control of the chemical-mechanical polishing process, the output of the light sensor being an input of said controller.

2. The apparatus according to claim 1, further comprising a gas product treatment portion having at least one input and at least one output, wherein an input of the gas product treatment portion is an output of the reaction chamber.

3. The apparatus according to claim 2 herein the reactive gas is ozone and the gas product treatment portion comprises an ozone scrubber.

4. The apparatus according to claim 2 wherein the reactive gas is ozone and the gas product treatment portion comprises an ozone scrubber, a vacuum pump and a silencer, each having at least one input and at least one output, wherein an input of the ozone scrubber is an output of the reaction chamber, an input of the vacuum pump is an output of the ozone scrubber and an output of the vacuum pump is an input of the silencer.

5. The apparatus according to claim 1 wherein the gas generator comprises an ozone generator having at least one input and at least one output, and an output of the gas generator is an input of the reaction chamber.

6. The apparatus according to claim 1 wherein the gas generator comprises an ozone generator and a gas drier, each having at least one input and at least one output, wherein an output of the ozone generator is an input of the reaction chamber and an output of the gas drier is an input of the ozone generator.

7. The apparatus according to claim 1, further comprising a carrier gas generator having at least one input and at least one output, wherein an output of the carrier gas generator is one an input of the catalytic converter.

\* \* \* \* \*